(12) United States Patent
Van Dortmont et al.

(10) Patent No.: US 8,507,729 B2
(45) Date of Patent: Aug. 13, 2013

(54) CYCLOHEXANONE PRODUCTION PROCESS WITH MULTIPLE POST-DISTILLATION

(75) Inventors: Godefridus Maria J. Van Dortmont, Grevenbicht (NL); Marleen Horsels, Munstergeleen (NL); Rudy Francois Maria Jozef Parton, Winkelse (BE); Johan Thomas Tinge, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 261 days.

(21) Appl. No.: 12/808,808

(22) PCT Filed: Dec. 16, 2008

(86) PCT No.: PCT/EP2008/067632
§ 371 (c)(1), (2), (4) Date: Sep. 16, 2010

(87) PCT Pub. No.: WO2009/080620
PCT Pub. Date: Jul. 2, 2009

(65) Prior Publication Data
US 2011/0028675 A1    Feb. 3, 2011

(30) Foreign Application Priority Data
Dec. 20, 2007 (EP) .................................. 07024765

(51) Int. Cl.
*C07C 45/82* (2006.01)
*B01J 8/00* (2006.01)

(52) U.S. Cl.
USPC ........................... 568/366; 422/187; 422/610

(58) Field of Classification Search
USPC ....................................................... 568/366
See application file for complete search history.

(56) References Cited

U.S. PATENT DOCUMENTS

| | | | |
|---|---|---|---|
| 2,829,166 A | 4/1958 | Joris et al. | |
| 3,305,586 A | 2/1967 | Bernard | |
| 4,272,326 A | 6/1981 | Hertzog et al. | |
| 4,306,944 A | 12/1981 | Murthy et al. | |
| 2006/0124441 A1 | 6/2006 | Benneker et al. | |

FOREIGN PATENT DOCUMENTS
EP    0 557 821    9/1993

OTHER PUBLICATIONS

International Search Report for PCT/EP2008/067632, mailed Feb. 20, 2009.
M.T. Musser: "Ullmann's Encyclopedia of Industrial Chemistry: Cyclohexanol and Cyclohexanone", 2005, Wiley-VCH, Weinheim, XP002482245.
Written Opinion of the International Searching Authority for PCT/EP2008/067632, mailed Feb. 20, 2009.

*Primary Examiner* — Sikarl Witherspoon
(74) *Attorney, Agent, or Firm* — Nixon & Vanderhye P.C.

(57) ABSTRACT

The present invention relates to a method for continuously preparing cyclohexanone from phenol making use of a catalyst comprising at least one catalytically active metal selected from platinum and palladium comprising hydrogenating phenol to form a product stream comprising cyclohexanone and unreacted phenol; separating at least part of the product stream, or at least part of the product stream from which one or more components having a lower boiling point than cyclohexanone have been removed, into a first fraction comprising cyclohexanone and a second fraction comprising phenol and cyclohexanol, using distillation; separating the second fraction into a third fraction, rich in cyclohexanol, and a fourth fraction, rich in phenol, using distillation; —subjecting at least part of the fourth fraction to a further distillation step, thereby forming a fifth fraction and a sixth fraction, wherein the fifth fraction is enriched in phenol compared to the sixth fraction, and wherein the sixth fraction comprises side-products having a higher boiling point than phenol, and phenol; and which method is characterized in the additional step of continuously or intermittently separating at least part of the sixth fraction to yet a further distillation step, thereby forming a seventh fraction and an eight fraction, wherein the seventh fraction is enriched in phenol compared to the eight fraction, and wherein the eight fraction comprises side-products having a higher boiling point than phenol.

15 Claims, 5 Drawing Sheets

CYCLOHEXANONE PRODUCTION PROCESS WITH MULTIPLE POST-DISTILLATION

This application is the U.S. national phase of International Application No. PCT/EP2008/067632, filed 16 Dec. 2008, which designated the U.S. and claims priority to European Application No. 07024765.5, filed 20 Dec. 2007, the entire contents of each of which are hereby incorporated by reference.

The invention relates to a method for the preparation of cyclohexanone from phenol and to a plant suitable for carrying out a method according to the invention.

Cyclohexanone can be employed as an industrial solvent or as an activator in oxidation reactions. It can also be used as an intermediate, inter alia in the production of adipic acid, cyclohexanone resins, caprolactam, nylon 6 or nylon 6,6.

Cyclohexanone is conventionally prepared from phenol by catalytic hydrogenation in a phenol hydrogenation reactor, e.g. using a platinum or a palladium catalyst. The reaction can be carried out in the liquid phase or the vapour phase. [Kirk-Othmer Encyclopedia of Chemical Technology, e.g. $3^{rd}$ Edition, Vol 7 (1979) p. 410-416; I. Dodgson et al. "A low Cost Phenol to Cyclohexanone Process", Chemistry & Industry, 18, December 1989, p 830-833; or M. T. Musser "Cyclohexanol and Cyclohexanone", Ullmann's Encyclopedia of Industrial Chemistry ($7^{th}$ Edition, 2007), (hereafter "Musser")].

In the preparation of cyclohexanone from phenol, typically cyclohexanol (which can be considered an intermediate product useful for further conversion to cyclohexanone) and various undesirable side-products are formed.

The cyclohexanone is typically recovered by a distillation process as a product rich in cyclohexanone (usually ≧90 wt. %) or as an essentially pure product (≧99 wt. %). In distillation, a fluid is separated into at least two fractions. When comparing two fractions, one may be called a "light" fraction, the other a "heavy" fraction. In particular when reference is made herein to a "light" fraction or a "heavy" fraction in relation to a separation by distillation, these terms are used herein relative to each other in a specific distillation step, to distinguish the fraction with the lower boiling point (the light fraction) from the fraction with the higher boiling point (the heavy fraction). Thus, a specific compound can be a "heavy" compound (mainly found in the heavy fraction) in a first distillation step, and a "light" compound (mainly found in the light fraction) in a second distillation step. As generally known, separation of a mixture into a heavy fraction and a light fraction is never absolute.

Figure 1:
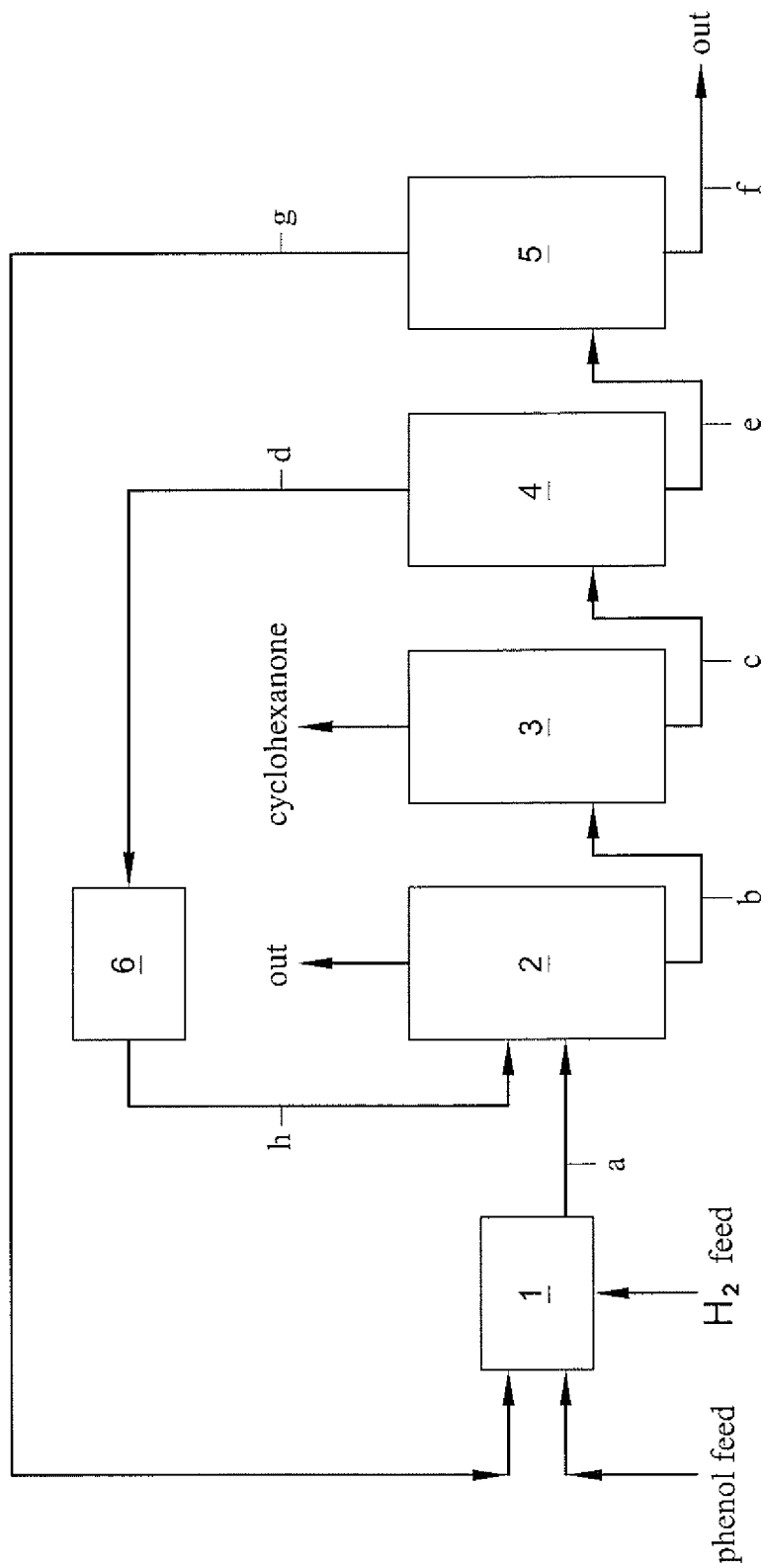

A conventional process for the preparation and recovery of cyclohexanone from phenol feedstock is schematically shown in FIG. 1.

Cyclohexanone is prepared in hydrogenation reaction section (1). This reaction section in particular comprises a hydrogenation reactor (which during use is supplied with hydrogen and phenol) and may comprise additional equipment. See for instance FIG. 1 in Musser, or in U.S. Pat. No. 3,305,586. The hydrogenation may either take place in a vapour phase process or in a liquid phase process.

Cyclohexanone, (unreacted) phenol and side-products, such as cyclohexanol is usually recovered from the stream leaving the reaction section using a number of distillation sections. A distillation section, as used herein is an installation comprising one distillation column or a plurality of distillation columns in parallel, each having the same functionality. Further this section may comprise other typical parts of distillation units.

In an optional first distillation section (2) (the pre-distillation section, i.e. a first part of a distillation section upstream of a distillation section wherein cyclohexanone is recovered) light components, e.g. benzene, cyclohexane, water are removed from the reaction product, which reaction product enters the distillation section (2) via conduit a and h, whereas cyclohexanone, residual phenol, cyclohexanol and other side-products leave the pre-distillation section as a bottom fraction via conduit b.

This bottom fraction is distilled in a second distillation section (3) (the main distillation section, i.e. wherein cyclohexanone is recovered). Herein cyclohexanone is recovered from the process stream as a light fraction. The heavy fraction of distillation section (3) contains residual phenol, cyclohexanol, various side-products, and in general still some cyclohexanone. This heavy fraction leaves the distillation section (3) via conduit c. Suitable distillation conditions are known in the art, see e.g. U.S. Pat. No. 2,829,166 or U.S. Pat. No. 3,076,810. From this heavy fraction, typically the valuable components residual phenol, cyclohexanol and cyclohexanone are recovered.

Cyclohexanol is typically recovered from this heavy fraction leaving the main distillation as a light fraction in a (first) post-distillation section (4) (post-distillation meaning downstream of the main distillation wherein cyclohexanone is recovered). This light fraction, which also contains some cyclohexanone, is a cyclohexanol-rich stream, usually comprising at least 70 wt. % cyclohexanol, in particular at least 80 wt. % cyclohexanol. This light fraction is subsequently led to a cyclohexanol dehydrogenation section (6) via conduit d (see e.g. Musser, paragraph 3.5). In cyclohexanol dehydrogenation section (6) cyclohexanol is partially dehydrogenated to form cyclohexanone. Typically, section (6) comprises a dehydrogenation reactor, and usually further an evaporator for evaporating the feed upstream of the reactor, and a condenser for condensing the product stream leaving the reaction. The cyclohexanone-enriched stream leaving section (6) is then led to pre-distillation section (2), via conduit h.

Phenol forms part of the bottom fraction of the first post-distillation. This bottom fraction is fed to a further post-distillation section (5), via conduit e, wherein remaining valuable components, mainly phenol and in general some cyclohexanone and some cyclohexanol, are recovered as the light fraction and returned to the phenol hydrogenation section, via conduit g. The bottom fraction from the last post-distillation is typically discarded via conduit f, e.g. incinerated or used for steam generation in a boiler house. Alternatively, the bottom fraction may be used as a low-cost material for a residual product, e.g. tar, asphalt, shoe polish or the like.

The inventors have realised that in the above described process, severe fouling with heavy residues occurs in post-distillation section (5). The energy consumption in post-distillation section (5) (for a given cyclohexanone production capacity) of the plant increases in time and the separation efficiency in post-distillation section (5) decreases in time. Therefore the plant has to be shut down frequently (four times a year, each time for two to four days) to clean post-distillation section (5). This results in a considerable loss of production.

It is an object of the invention to provide a method for preparing cyclohexanone, wherein one or more of the above drawbacks are overcome or at least alleviated.

The inventors have found that it is possible to increase production capacity, reduce energy consumption and/or reduce fouling in a process for converting phenol to cyclohexanone by hydrogenation by introducing an additional separation step.

Accordingly, the present invention relates to a method for continuously preparing cyclohexanone from phenol making use of a catalyst comprising at least one catalytically active metal selected from platinum and palladium comprising the steps of
- a) hydrogenating phenol to form a product stream comprising cyclohexanone and unreacted phenol;
- b) separating at least part of the product stream, or at least part of the product stream from which one or more components having a lower boiling point than cyclohexanone have been removed, into a first fraction comprising cyclohexanone and a second fraction comprising phenol, cyclohexanol, using distillation;
- c) separating the second fraction into a third fraction, rich in cyclohexanol, and a fourth fraction, rich in phenol, using distillation;
- d) subjecting at least part of the fourth fraction to a further distillation step, thereby forming a fifth fraction and a sixth fraction, wherein the fifth fraction is enriched in phenol compared to the sixth fraction, and wherein the sixth fraction comprises side-products having a higher boiling point than phenol, and phenol; and is characterized in the additional step of
- e) continuously or intermittently separating at least part of the sixth fraction to yet a further distillation step, thereby forming a seventh fraction and an eight fraction, wherein the seventh fraction is enriched in phenol compared to the eight fraction, and wherein the eight fraction comprises side-products having a higher boiling point than phenol.

The invention further relates to a chemical plant suitable for carrying out a method according to the invention, the plant (see FIGS. 2A, 2B, 3A and 3B) comprising
- a phenol hydrogenation reaction section (1);
- downstream of the phenol hydrogenation reaction section (1) a plurality of distillation sections, optionally including a pre-distillation section (2), for removing one or more light components from the product stream from the hydrogenation section and comprising sections (3), (4), (5), (7) respectively for separating the product stream of the phenol hydrogenation reaction section (1) into a first fraction (to be led out of the section (3) via conduit "cyclohexanone") and a second fraction (to be led to section (4) via conduit c), for separating said second fraction into a third fraction (to be led out of section (4) via conduit d) and a fourth fraction (to be led to section (5) via conduit e), for separating said fourth fraction into a fifth fraction (to be led out of section (5) via conduit g) and a sixth fraction (to be led to section (7) via conduit t), and for separating said sixth fraction into a seventh fraction (to be led out of section (7) via i (FIGS. 2B and 3A) or i' (FIGS. 2B and 3B)) and an eight fraction (to be led out of section 7 via conduit j, usually an outlet out of the plant).

Usually, the plant comprises a loop (comprising conduit d, dehydrogenation section (6), and conduit h) for converting at least part of the cyclohexanol in said third fraction from distillation section (4) into cyclohexanone and feeding the resulting stream into distillation section (2). Moreover, the plant usually comprises a recycling loop (comprising conduit g) for recycling at least part of said fifth fraction into hydrogenation section 1.

Figure 2A:
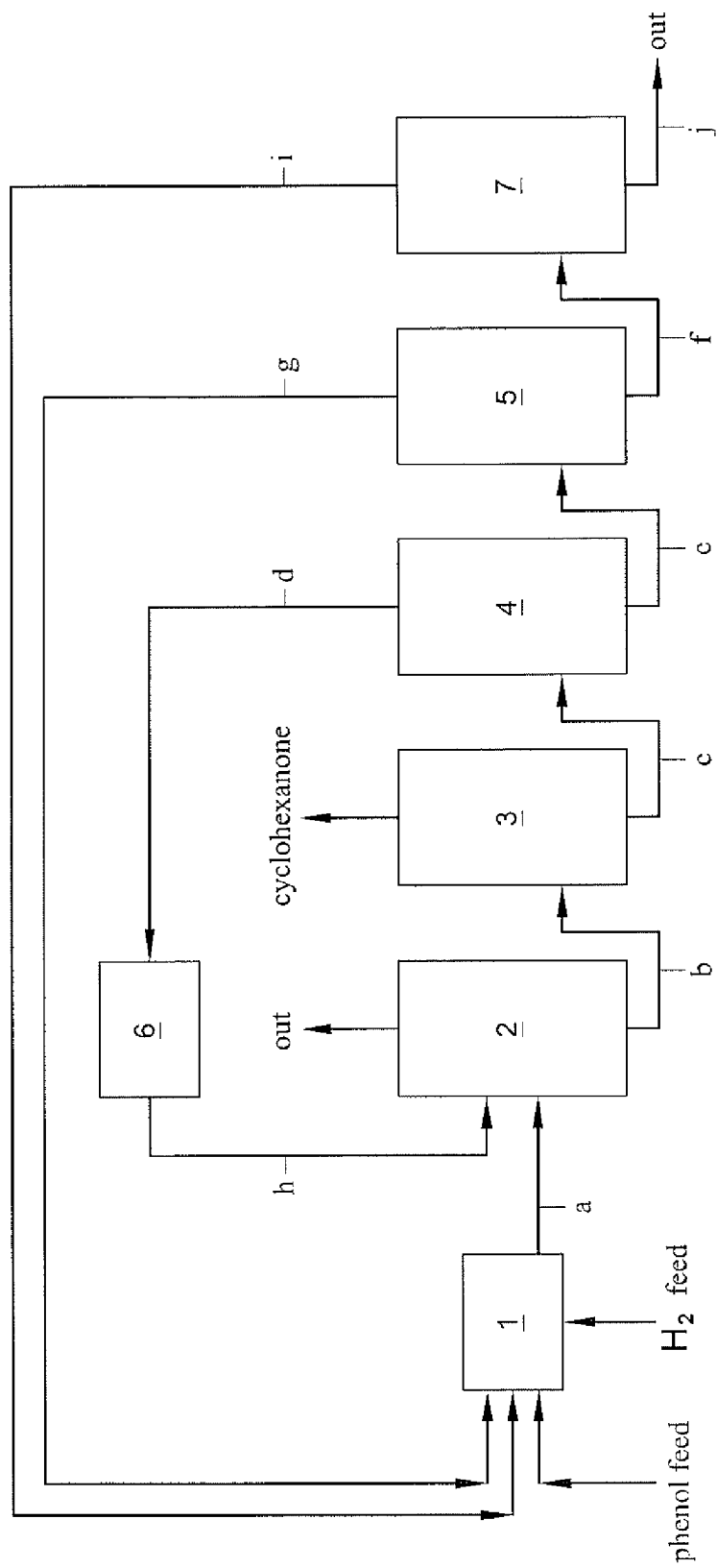
Figure 2B:
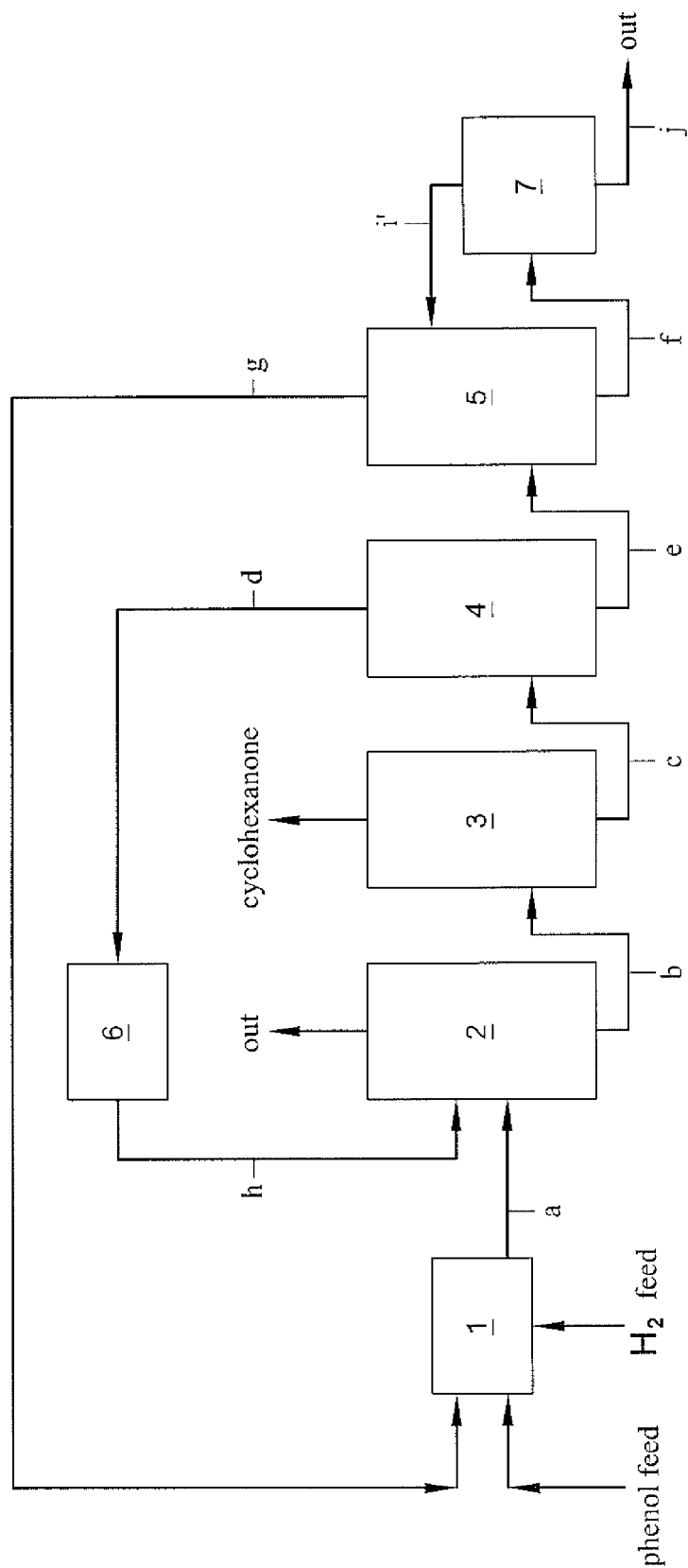
Figure 3A:
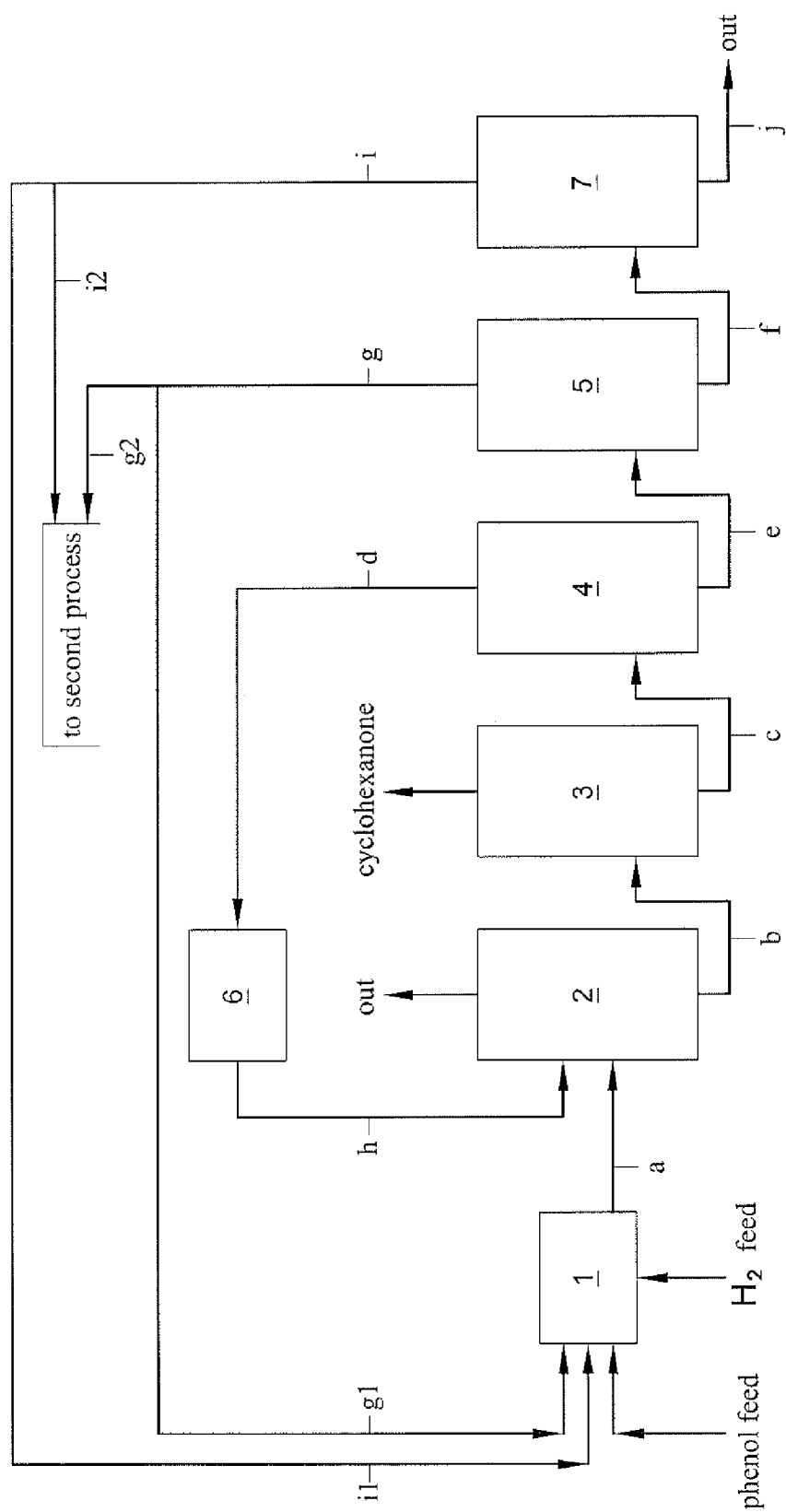
Figure 3B:
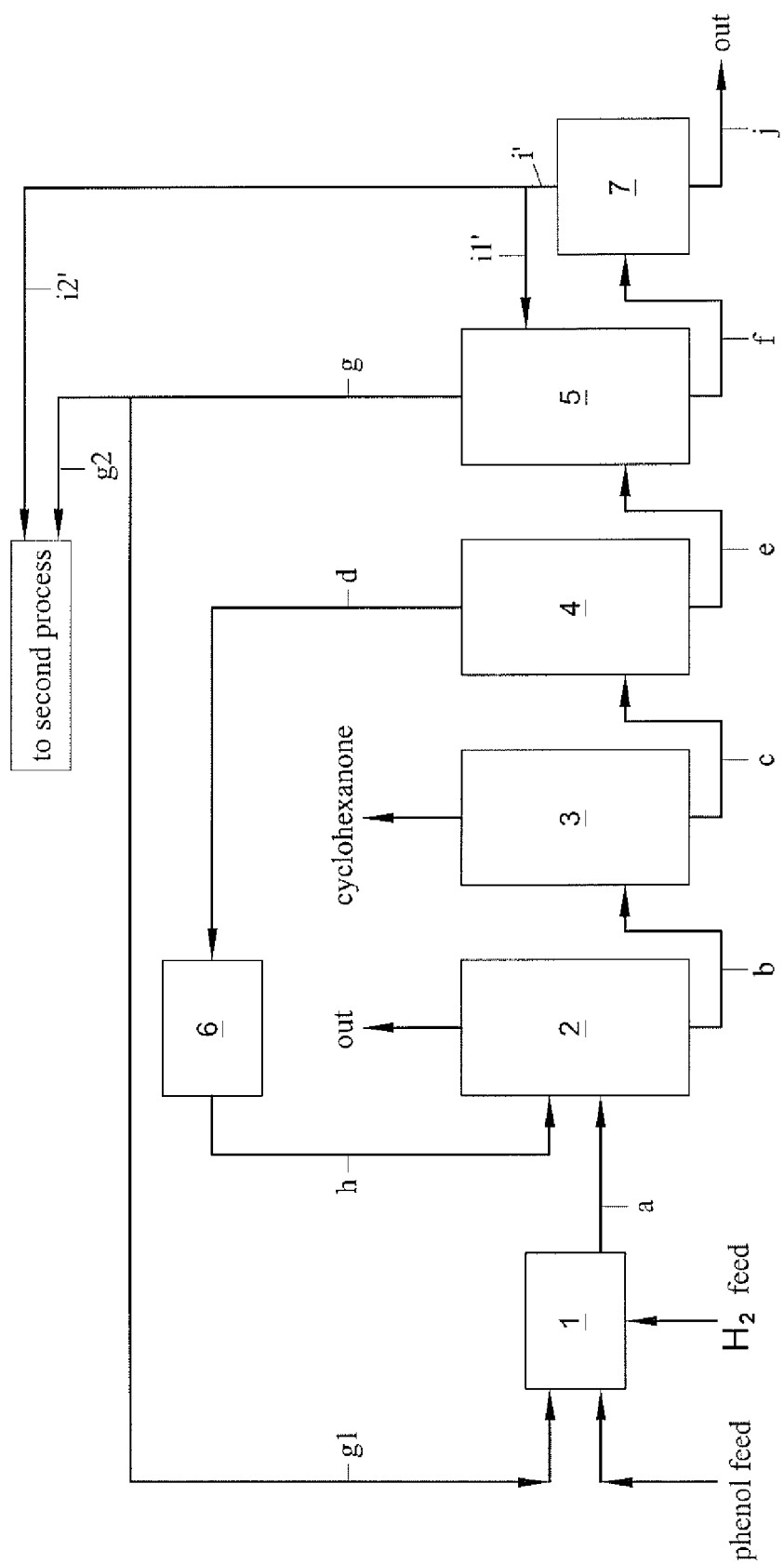

Preferably, the plant also comprises a recycling loop for recycling at least part of said seventh fraction i from distillation section (7) into hydrogenation section (1) (FIGS. 2A and 3A) or a recycling loop for recycling at least part of said seventh fraction i' to post-distillation (5) (FIGS. 2B and 3B).

FIG. 1 schematically shows a conventional installation for preparing cyclohexanone from phenol feedstock.

FIG. 2A schematically shows a plant according to the invention, wherein (a) recycling loop(s) is/are present for recycling the fifth and/or seventh fraction to hydrogenation section (1).

FIG. 2B schematically shows a plant according to the invention, wherein a recycling loop is present for recycling the seventh fraction to distillation section (5), and wherein a recycling loop is present for recycling the fifth fraction to hydrogenation section 1.

FIG. 3A schematically shows a plant according to the invention wherein a conduit is present for leading the seventh and/or fifth fraction or part of any of these fractions into hydrogenation section (1) and/or into an installation for carrying out another process.

FIG. 3B schematically shows a plant according to the invention wherein a recycling loop is present for recycling the seventh fraction or part thereof to distillation section (5), and/or for feeding the seventh fraction into an installation for carrying out another process, and wherein also a conduit is present for leading the fifth fraction or part thereof into hydrogenation section (1) and/or into an installation for carrying out another process.

As will be understood by the skilled person, the embodiments illustrated as examples in FIGS. 2A, 2B, 3A and 3B, discussed herein below in more detail, or parts thereof may be combined to provide alternative embodiments of the invention. It is to be noted that in these Figures feed streams to numbered sections are represented as separate streams, but it will be evident to the skilled person that streams fed into a section may be combined before entering the section, or may enter the section separately. E.g. streams fed into a section may be introduced into a distillation column of the section at different levels of the column.

In a method of the invention, production capacity is increased (because of less down time, and less fouling) and energy losses (due to fouling) are decreased. In particular, the inventors found that a plant, e.g. as schematically shown in FIGS. 2A, 2B, 3A and 3B, wherein a method of the invention is carried out does not need to be shut down anymore for cleaning a distillation section, in particular section (5) as shown in the Figures, or at least not as often. This is accomplished by an extra post-distillation step (distillation section (7)). Also separation efficiency may be increased. Due to the extra post-distillation step f), post-distillation step e) (cf. section (5) in the Figures) requires less energy input. Because relatively more phenol will be present in the bottom of section (5), the temperature and residence time of the liquid in the bottom of post-distillation column (5) will significantly be reduced, and consequently the amount of heavy residues produced therein is significantly lower. Accordingly, fouling of section (5) is strongly reduced.

In a method according to the invention, the bottom fraction of post-distillation section (5) is fed to a further post-distillation section (7), via conduit f, wherein remaining valuable components, mainly phenol and in general some cyclohexanone and some cyclohexanol, may be recovered as the light fraction and—if desired—returned to the phenol hydrogenation section (1), via conduit i (FIGS. 2A and 3A) or to post-distillation section (5), via conduit i' (FIGS. 2B and 3B). The bottom fraction of the last post-distillation section (7) is typically discarded via conduit j (out), e.g. incinerated or used for steam generation in a boiler house. Alternatively, the bottom fraction may be used as a low-cost material for a residual product, e.g. tar, asphalt, shoe polish or the like. Due to just partial removal of phenol in post-distillation section (5), the bottom temperature and liquid residence time in post-distillation section (5), wherein step e) is carried out, is reduced resulting in less heavy residue formation and therefore less fouling in post-distillation section (5).

According to the present invention, fouling of post-distillation section (5) can even be reduced to such extent that it does not need to be cleaned for a period of several years. It is noted that post-distillation section (7), wherein step f) is carried out, may need to be cleaned from time to time, e.g. two times per year or less, but during such cleaning of post-distillation section (7) the plant can be operated as the conventional process, i.e. without step f). Thus the plant does not have to be shut down. Accordingly, during part of the time the cyclohexanone plant comprising steps a), c), d), e) and optionally step b) can be carried out, while step f) is omitted (and the section wherein step f) is carried out can suitably be cleaned). Although, according to the invention, the post-distillation section (7), step f), is not necessarily in use continuously for recovery of phenol, post-distillation section (7) is usually on stream for recovery of phenol for at least 90% of the run-time, more preferably for at least 95% of the time.

Accordingly, the process of the invention can be carried out continuously, without needing to shut down the plant for cleaning of post-distillation section (5). Thus the number of shut downs can be limited to those shut downs required e.g. by governmental regulations and/or for regular plant maintenance and/or for replacement of catalyst, in total usually about once every 4 years.

Thus, the present invention allows the continuous production of cyclohexanone for a prolonged time, compared to a conventional method as described above. The reduced fouling by the implementation of the further post-distillation step f) improves the energy and separation efficiency of the cyclohexanone process. Moreover additional plant shut downs for cleaning are avoided resulting in significantly increased production capacity.

When referred herein to a stream, a product or other composition, "rich in" or "enriched in" a specific component, this generally means that this component is the major component, and in particular that the component is present in a concentration of more than 50 wt. %. However, this lower limit may be different for specific streams and components.

In general, the first fraction is rich in cyclohexanone, and enriched in cyclohexanone compared to the product stream. Preferably, the first fraction comprises at least 99 wt. % cyclohexanone, more preferably at least 99.8 wt. % cyclohexanone.

The third fraction, rich in cyclohexanol, may in particular be a light fraction of the distillation step wherein the third fraction is formed, whereas the fourth fraction may in particular be a heavy fraction. The third fraction preferably comprises at least 70 wt. %, more preferably at least 80 wt. % cyclohexanol. The fourth fraction preferably comprises at least 65 wt. % phenol.

The fifth fraction, having a higher phenol content than the fourth fraction, will in particular be a light fraction of the distillation step wherein the fourth fraction is distilled, whereas the sixth fraction will in particular be a heavy fraction. The sixth fraction has a lower phenol content than the fourth fraction. The phenol concentration in the sixth fraction is preferably at least 20 wt. % and more preferably at least 25 wt. % phenol. A relatively high phenol concentration in the sixth fraction is advantageous, because enhanced phenol concentration reduces the boiling point of the sixth fraction, and formation of polymeric side-products (which are highly contributing to the fouling) is reduced.

The seventh fraction may in particular be a light fraction of the distillation step wherein the seventh fraction is formed, whereas the eighth fraction may in particular be a heavy fraction. The seventh fraction preferably comprises at least 40 wt. %, more preferably at least 60 wt. % phenol. The eighth fraction, usually a small fraction, preferably comprises less than 25 wt. % phenol and more preferably less than 20 wt % phenol.

Step b) may also be referred to as a pre-distillation step, step c) as the main distillation step (as cyclohexanone is recovered in this step). Step d), e) and f) may also be referred to as a first, a second and a third post-distillation step, respectively.

One or more of the fractions from the post-distillation steps that are enriched in phenol may fully or partially be recycled, in particular to the hydrogenation step a) or from step f) to step e) (from the third post-distillation section (7) to the second post-distillation section (5) in the Figures showing embodiments according to the invention). It is also possible to lead such a fraction or a part thereof and/or the fifth fraction or a part thereof into a second process, different from the process for preparing cyclohexanone from phenol, as will be described in more detail below.

The hydrogenation of phenol can in principle be carried out in any way, in a vapour phase or in a liquid phase, e.g. based on any technology described in or referred to in Kirk-Othmer Encyclopedia of Chemical Technology $3^{rd}$ Edition, Vol 7, 1979 p. 410-416; I. Dodgson et al. "A low Cost Phenol to Cyclohexanone Process", Chemistry & Industry, 18, Dec. 1989, p 830-833; GB 890,095; Hancil and Beranek Chem. Eng. Sci., 25, 1970, p. 1121-1126; or Sakai et al. Nippon Kagaku Kaishi, 5, 1972, 821-829; Musser (in Ullmans's, see above); U.S. Pat. No. 2,829,166 or U.S. Pat. No. 3,076,810. The hydrogenation reaction section may comprise an internal recycling stream for recycling part of the stream leaving a reactor wherein the hydrogenation takes place. Product stream leaving the hydrogenation reaction section generally comprises cyclohexanone, cyclohexanol, phenol and side-products.

The distillation steps (pre-distillation, main distillation, and post-distillations) can be accomplished in a manner known in the art, per se. Suitable distillation conditions can routinely be determined by the skilled person, based on common general knowledge and optionally some routine testing. In particular the skilled person may consult the prior art cited herein. For step f) respectively section (7), a conventional distillation column can be used, e.g. a distillation column as described in the art for the preceding post-distillation steps. It is also possible to use a more simple distillation apparatus, such as a film-evaporator, in particular a one-pass film evaporator. A film-evaporator shows sufficient separation efficiency for suitably carrying out step f) and is particularly advantageous in that it reduces investments and that its simple design allows faster cleaning.

As indicated above, the process of the invention comprises the synthesis of cyclohexanone and a number of distillation steps, inter alia to recover cyclohexanone.

As shown in FIGS. 2A and 2B, the hydrogenation step a), optional pre-distillation step b), main distillation step c) and post-distillation steps d) and e) may be carried out as generally described above, when discussing FIG. 1. In accordance with the embodiments of the invention as schematically shown in FIGS. 2A and 2B, conduit f is no longer used as an outlet of the process (as present in an embodiment according to FIG. 1), but is arranged to lead the bottom fraction from post-distillation section (5) into post-distillation section (7). Conduit i is arranged to recycle the light fraction of post-distillation section (7) to hydrogenation section (1) (FIG. 2A), whereas conduit i' is used to recycle the light fraction of post-distillation section (7) to post-distillation section (5) (FIG. 2B). Outlet j is provided for discharging the heavy fraction from post-distillation section (7). However, it is also possible to provide that conduit j is used for leading the heavy fraction from post-distillation section (7) into a yet further post-distillation section (not shown).

In FIG. 3a conduit i is split into conduit i1 arranged to recycle at least part of the light fraction from post-distillation section (7) to hydrogenation section (1) and conduit i2, arranged to lead the light fraction or part thereof into an installation for carrying out a second process. It is also possible to omit conduit i1. Optionally conduit g (for the light fraction from post-distillation section (5)) is split into conduits g1, for recycling said light fraction or a part thereof to hydrogenation section (1), and g2, for leading said light fraction of a part thereof into a second process different from the process for preparing cyclohexanone from phenol.

FIG. 3B schematically shows an installation, wherein a recycling loop i1' from post-distillation section (7) to post-distillation section (5) is present and wherein conduit i2' is present for leading the light fraction from post-distillation section (7), or part thereof, into a second process different from the process for preparing cyclohexanone from phenol.

As the second process, in principle any process can be used wherein use can be made of such fraction. In particular suitable second processes include phenol-formaldehyde resin production processes. Accordingly, conduits i2 and i2', and/or conduit g2 may in particular lead to a phenol-formaldehyde resin installation.

Alternatively or in addition, conduits d and/or h may be arranged to fully or partially leading a light fraction from post-distillation section (4), a light fraction from post-distillation section (5), respectively a product stream from section (6) into another process. In particular, any such other process can be used wherein cyclohexanol is a suitable reagent for producing the substance of interest, wherein cyclohexanol is a suitable solvent or wherein cyclohexanol is the substance of interest. Such other process may in particular be selected from the group of cyclohexane oxidation processes, cyclohexanol dehydrogenation processes, and adipic acid production processes.

The invention will now be illustrated by the following examples.

EXAMPLES

The comparative experiment was carried out in a conventional plant wherein cyclohexanone is produced by hydrogenation of phenol, as schematically depicted in FIG. 1. For convenience of comparison with the examples according to the invention, the actual plant data were scaled to an annual plant capacity of 100 000 metric tons of essentially pure cyclohexanone. For the examples according to the invention, results are presented which were obtained by simulating a 100 000 metric tons per year plant modified according to the invention, as described below. The main unit of post-distillation section 5 (in the comparative experiment and in the Examples) is a distillation column with a diameter of 1 m and a height of 15 m. The vapour leaving the top of this column is liquefied in a condenser. Part of the obtained liquid is fed to the top of this column as reflux, and the other part, flow g, is led to the phenol hydrogenation section (1). The required energy for the distillation process in the column is introduced by means of indirect heating via steam. Flow f containing amongst others side-products, phenol, cyclohexanone and cyclohexanol leaves the process via the bottom of the distillation column of post-distillation section (5).

In Example I (according to the invention), an additional post-distillation section (7) is added to the purification part of the cyclohexanone plant (as shown in FIG. 2A). In this case the bottom flow f of post-distillation section (5) does not leave the process, but is used as feed to post-distillation section (7). The main unit of post-distillation section (7) is a distillation column with a diameter of 0.7 m and a height of 15 m. The vapour leaving the top of this column is liquefied in a condenser. Part of the obtained liquid is fed to the top of the column as reflux, and the other part, flow i, is fed to the phenol hydrogenation section (1). The required energy for the distillation process in the column is introduced by means of indirect heating via steam. Flow j containing amongst others side-products, phenol, cyclohexanone and cyclohexanol leaves the plant via the bottom of the distillation column of post-distillation section (7).

Example II (according to the invention) differs from Example I in that the additional post-distillation section (7), comprises a one-pass film evaporator instead of the distillation column. The plant set-up for Example II is schematically depicted in FIG. 2B. In this case the bottom flow f of post-distillation section (5) is used as feed of post-distillation section (7). The main unit of post-distillation section (7) now is a one-pass film evaporator with a diameter of 0.5 m and a height of 5.4 m. The feed f is introduced at the top of the evaporator. The vapour leaving the top of one-pass film evaporator, flow i, is fed to post-distillation section (5). The required energy for the one-pass film evaporator of post-distillation section (7) is introduced by means of indirect heating via steam. The heavy stream j leaving the film evaporator of post-distillation section (7) contains—amongst others—side-products, phenol, cyclohexanone and cyclohexanol.

Comparative Experiment

The cyclohexanone plant, consisting of a phenol hydrogenation section, a recovery/purification section and a cyclohexanol converter section, as described before and depicted in FIG. 1, directly after cleaning of the whole plant including the bottom section and the reboiler of the distillation column in section (5), theoretically can be operated (if the production level reached directly after cleaning could be maintained without shut downs) at an annual production capacity of 100 000 metric tons of essentially pure cyclohexanone.

The distillation conditions in post-distillation section (5) were:

reflux ratio: 1.3.
heat duty of the reboiler: 0.40 MW.

Under these conditions, the following performance of the distillation column in post-distillation section (5) is observed one week after start-up:

| Flow | e | f | g |
|---|---|---|---|
| Mass flow (in kg per hour): | 1162 | 84 | 1078 |
| Composition (in mass fractions): | | | |
| cyclohexanone | 0.033 | 0.018 | 0.034 |
| cyclohexanol | 0.169 | 0.010 | 0.181 |
| phenol | 0.740 | 0.161 | 0.785 |
| residue | 0.058 | 0.811 | 0.000 |

However, due to fouling of the bottom section, of the sieves in the pumps and of the reboiler of the distillation column in post-distillation section (5) separation and energy efficiency are deteriorating over time.

In order to maintain adequate operation of the plant, the plant had to be shut down every 3 months for a period of 2-4 days to remove the fouling of the distillation column in post-distillation section (5). As a consequence of the fouling and the shut downs for cleaning a loss in the actual annual production capacity of the cyclohexanone plant of over 3600 metric tons/year can be calculated.

Example I

The cyclohexanone plant, consisting of a phenol hydrogenation section, a recovery/purification section and a cyclohexanol converter section, as described before and as depicted in FIG. 2A, directly after start-up of the clean plant, theoretically can be operated at an annual production capacity of 100 000 metric tons of essentially pure cyclohexanone.

The distillation conditions in post-distillation section (5) were:
reflux ratio: 1.14.
reboiler duty: 0.30 MW.

The distillation conditions in post-distillation section (7) were:
reflux ratio: 2.1.
reboiler duty: 0.11 MW.

Under these conditions the following performance of the distillation columns in post-distillation sections (5) and (7) will be present:

| Flow | e | j | g | f | i |
|---|---|---|---|---|---|
| Mass flow (in kg per hour): | 1162 | 84 | 876 | 286 | 202 |
| Composition (in mass fractions): | | | | | |
| cyclohexanone | 0.033 | 0.018 | 0.020 | 0.072 | 0.093 |
| cyclohexanol | 0.169 | 0.010 | 0.194 | 0.091 | 0.126 |
| phenol | 0.740 | 0.161 | 0.786 | 0.600 | 0.780 |
| residue | 0.058 | 0.811 | 0.000 | 0.237 | 0.000 |

During a period of four years of operation of this cyclohexanone plant, the whole plant, including post-distillation section (5), could be operated continuously at full production capacity without shutting down of the whole plant for cleaning, but with only few (twice per year) short cleanings of post-distillation section (7). However, during these periods of cleaning of post-distillation section (7), the production of essentially pure cyclohexanone could be continued at full capacity, because the other parts of the cyclohexanone plant could remain to be operated as described in the Comparative Experiment. Therefore, the gain in production capacity was about 3600 metric tons/year, compared to the conventional method as described in the Comparative Experiment.

Example II

The cyclohexanone plant, consisting of a phenol hydrogenation section, a recovery/purification section and a cyclohexanol converter section, as described before and as depicted in FIG. 2B, directly after start-up of the clean plant theoretically can be operated at an annual production capacity of 100 000 metric ton of cyclohexanone as final product.

The distillation conditions in post-distillation section (5) were:
reflux ratio: 1.3.
reboiler duty: 0.35 MW The distillation conditions in post-distillation section (7) were:
energy duty: 0.05 MW.

Under these conditions the following performance of the distillation columns in post-distillation sections (5) and (7) was reached:

| Flow | e | j | g | f | i |
|---|---|---|---|---|---|
| Mass flow (in kg per hour): | 1162 | 84 | 1078 | 507 | 423 |
| Composition (in mass fractions): | | | | | |
| cyclohexanone | 0.033 | 0.018 | 0.034 | 0.053 | 0.060 |
| cyclohexanol | 0.169 | 0.010 | 0.181 | 0.029 | 0.033 |
| phenol | 0.740 | 0.161 | 0.785 | 0.350 | 0.387 |
| residue | 0.058 | 0.811 | 0.000 | 0.568 | 0.520 |

During a period of four years of operation in this cyclohexanone plant, the whole plant including post-distillation section (5) could be operated continuously at full production capacity without shutting down of the whole plant for cleaning, but with only few (twice per year) short cleanings of the one-pass film evaporator (7). However, during these periods of cleaning of the one-pass film evaporator (7), the production of cyclohexanone could be continued at full capacity, because the other parts of the cyclohexanone plant could remain to be operated as described in the Comparative Experiment. Therefore the gain in production capacity was about 3600 metric tons a year, compared to the conventional method as described in the Comparative Experiment.

The invention claimed is:

1. A method for continuously preparing cyclohexanone from phenol making use of a catalyst comprising at least one catalytically active metal selected from platinum and palladium comprising the steps of:
   a) hydrogenating phenol to form a product stream comprising cyclohexanone and unreacted phenol;
   b) separating at least part of the product stream, or at least part of the product stream from which one or more components having a lower boiling point than cyclohexanone have been removed, into a first fraction comprising cyclohexanone and a second fraction comprising phenol and cyclohexanol, using distillation;
   c) separating the second fraction into a third fraction, rich in cyclohexanol, and a fourth fraction, rich in phenol, using distillation;
   d) subjecting at least part of the fourth fraction to a further distillation step, thereby forming a fifth fraction and a sixth fraction, wherein the fifth fraction is enriched in phenol compared to the sixth fraction, and wherein the sixth fraction comprises side-products having a higher boiling point than phenol, and phenol; and
   e) continuously or intermittently separating at least part of the sixth fraction to yet a further distillation step, thereby forming a seventh fraction and an eight fraction, wherein the seventh fraction is enriched in phenol compared to the eight fraction, and wherein the eight fraction comprises side-products having a higher boiling point than phenol.

2. The method according to claim 1, wherein at least part of the fifth fraction, at least part of the seventh light fraction comprising phenol, or at least part of both said fifth fraction and said seventh light fraction is continuously or intermittently recycled to step a).

3. The method according to claim 1, wherein at least part of the seventh fraction is recycled to step e).

4. The method according to claim 1, wherein at least part of the fifth fraction, at least part of the seventh light fraction comprising phenol, or at least part of both said fifth fraction and said seventh light fraction is continuously or intermittently introduced into a second process different from the process for preparing cyclohexanone from phenol.

5. The method according to claim 4, wherein the second process is a process for preparing a formaldehyde-phenol resin.

6. The method according to claim 1, wherein the at least part of the third fraction is continuously or intermittently introduced into a second process different from the process for preparing cyclohexanone from phenol.

7. The method according to claim 6, wherein the second process is a cyclohexane oxidation process, in which cyclohexanol and/or cyclohexanone is produced from cyclohexane.

8. The method according to claim 6, wherein the second process is a cyclohexanol dehydrogenation process, comprising use of a cyclohexanol converter in which the cyclohexanol is at least partially converted into cyclohexanone, wherein thereafter in the second process cyclohexanone is separated from residual cyclohexanol and recycling sideproduct originating from the first process.

9. The method according to claim 6, wherein the second process is an adipic acid production process, wherein cyclohexanol is converted into adipic acid.

10. A chemical plant suitable for carrying out a method according to claim 1, comprising
a phenol hydrogenation reaction section (1);
downstream of the phenol hydrogenation reaction section (1) a plurality of distillation sections, optionally including a pre-distillation section (2) and comprising sections (3), (4), (5), and (7) respectively for separating the product stream of the phenol hydrogenation reaction section (1) into a first cyclohexanone fraction and a second fraction (c), for separating said second fraction into a third fraction (d) and a fourth fraction (e), for separating said fourth fraction into a fifth fraction (g) and a sixth fraction (f), and for separating said sixth fraction into a seventh fraction (i,i'), and an eight fraction (j).

11. The chemical plant according to claim 10, wherein the plant downstream of section (1) comprises a pre-distillation section (2) for removing one or more light components from the product stream leaving section (1), and further comprises a loop for converting at least part of the cyclohexanol in the third fraction into cyclohexanone and feeding the resulting stream into predistillation section (2), and optionally also comprising a recycling loop for recycling at least part of the fifth fraction into hydrogenation section (1).

12. The chemical plant according to claim 10, comprising a recycling loop for recycling at least part of a light fraction formed in the distillation section (7) for forming the seventh and the eight fraction, to the distillation section (5) for forming the fifth and the sixth fraction.

13. The chemical plant according to claim 10, wherein the distillation section (7) for forming the seventh and the eight fraction comprises a film evaporator.

14. The chemical plant according to claim 10, comprising a conduit for leading at least one fraction or a part thereof selected from the group of light fraction from at least one of the post-distillation sections (4), (5) and (7) to a different installation, different from the process for preparing cyclohexanone from phenol.

15. The chemical plant according to claim 14, wherein the different installation is an installation selected from the group consisting of installations for dehydrogenating cyclohexanol, installations for preparing adipic acid, installations for oxidising cyclohexane and installations for preparing a formaldehyde-phenol resin.

* * * * *